(12) United States Patent
Tashenov

(10) Patent No.: US 11,083,424 B2
(45) Date of Patent: Aug. 10, 2021

(54) ANTI-SCATTER GRID FOR A MEDICAL X-RAY IMAGING SYSTEM

(71) Applicant: Siemens Healthcare GmbH, Erlangen (DE)

(72) Inventor: Stanislav Tashenov, Heroldsbach (DE)

(73) Assignee: Siemens Healthcare GmbH, Erlangen (DE)

( * ) Notice: Subject to any disclaimer, the term of this patent is extended or adjusted under 35 U.S.C. 154(b) by 13 days.

(21) Appl. No.: 16/586,492

(22) Filed: Sep. 27, 2019

(65) Prior Publication Data

US 2020/0100737 A1 Apr. 2, 2020

(30) Foreign Application Priority Data

Sep. 28, 2018 (DE) .................. 10 2018 216 805.9

(51) Int. Cl.
*A61B 6/00* (2006.01)
*G21K 1/02* (2006.01)
*A61B 6/03* (2006.01)
*A61B 6/08* (2006.01)

(52) U.S. Cl.
CPC ............ *A61B 6/4291* (2013.01); *G21K 1/025* (2013.01); *A61B 6/032* (2013.01); *A61B 6/08* (2013.01); *A61B 6/5282* (2013.01); *A61B 6/584* (2013.01)

(58) Field of Classification Search
CPC .............................. A61B 6/4291; G21K 1/025
See application file for complete search history.

(56) References Cited

U.S. PATENT DOCUMENTS

| 5,099,134 A * | 3/1992 | Hase ................. G21K 1/025 378/154 |
| 2006/0098784 A1* | 5/2006 | Bacher ................ G21K 1/00 378/154 |

FOREIGN PATENT DOCUMENTS

| DE | 632098 C | 7/1936 |
| DE | 102005050487 A1 | 5/2006 |

* cited by examiner

*Primary Examiner* — Chih-Cheng Kao
(74) *Attorney, Agent, or Firm* — Lempia Summerfield Katz LLC

(57) ABSTRACT

An anti-scatter grid for an X-ray beam detector is provided. The anti-scatter grid includes a plurality of X-ray absorption plates and a carrier body to which the plurality of X-ray absorption plates are fastened. The carrier body is embodied in a meander shape with a plurality of linearly extending subsections and curve sections connecting the plurality of linearly extending subsection with one another. At least one X-ray absorption plate is arranged in each linearly extending subsection of the plurality of linearly extending subsections.

15 Claims, 3 Drawing Sheets

ANTI-SCATTER GRID FOR A MEDICAL X-RAY IMAGING SYSTEM

This application claims the benefit of DE 10 2018 216 805.9, filed on Sep. 28, 2018, which is hereby incorporated by reference in its entirety.

BACKGROUND

The present embodiments relate to an anti-scatter grid for a medical X-ray imaging system.

X-ray imaging systems (e.g., X-ray units) typically include an X-ray beam source and an X-ray beam detector (e.g., X-ray detector) that are arranged opposite one another. During operation of the X-ray unit, the X-ray radiation emitted by the X-ray beam source and partially attenuated by a measurement subject (e.g., a patient) is detected by the X-ray detector. The X-ray detector is configured to output a signal (e.g., a measurement signal) corresponding to the intensity of the incident X-ray radiation. For example, the X-ray detector includes a plurality of picture elements (e.g., "pixels") that serve for detecting the intensity distribution of the incident X-ray radiation in a two-dimensionally resolved manner. In such an arrangement, the X-ray detector is optionally subdivided into multiple detector elements, each of which includes a plurality of pixels. By this, it is also easily possible to form large-scale as well as curved X-ray detectors (e.g., for application in computed tomography) by corresponding arrangement of the detector elements along one or more axes (e.g., "tiling").

Due to different physical effects during operation of the X-ray unit, the X-ray radiation emitted by the X-ray radiation source is not only attenuated to different degrees by the measurement subject as a function of the beam direction, but is also partially scattered at an angle to the original radiation direction, which typically extends radially to the X-ray radiation source. Due to overlapping with the X-ray beams (e.g., primary X-ray beams) impinging in the original radiation direction, the scattered rays (e.g., "radiation scatter"), upon impacting the X-ray detector, cause a distortion of the image reconstructed from the intensity distribution. For example, the scattered rays lead to a reduction in the contrast and, in certain circumstances, also in the spatial resolution of the reconstructed image.

In order to reduce the effects of the scattered rays, an X-ray detector is often assigned a device known as an anti-scatter grid (e.g., a "scatter removal grid") that is positioned in front of the X-ray-sensitive elements of the X-ray detector in the radiation direction. In most cases, anti-scatter grids of the type feature a grid-like structure, with each grid aperture forming a kind of radiation channel running in the direction of the primary X-ray beams. In such an arrangement, the individual radiation channels are separated from one another by walls that are formed from a material that is, for example, highly X-ray absorbing, such as, for example, lead or tungsten. In most cases, each radiation channel is therein assigned to a single pixel or at least to a small number of pixels. The radiation channels are furthermore elongated. In other words, the radiation channels are embodied with a length that is multiple times greater in the direction of the primary X-ray beams than an extension transverse to the direction of the primary X-ray beams. What is achieved as a result is that scattered rays diverging from the direction of the primary X-ray beams strike the walls bordering the radiation channels and are adsorbed thereby.

Typically, anti-scatter grids also absorb a portion of the unscattered X-ray radiation that may no longer be detected by the X-ray detector. This absorption takes place only at the walls of the individual radiation channels. In this way, the absorption of the non-scattered X-ray radiation produces an X-ray intensity modulation that becomes visible through regular streaks in the reconstructed X-ray image.

One solution for this problem consists in making the dimensions of the radiation channels smaller than those of a detector pixel. However, this embodiment requires an elaborate and complex design for the anti-scatter grid, which may furthermore impair the absorption of scattered X-ray radiation.

Another solution for this problem includes increasing the size of the radiation channels of the anti-scatter grid across multiple pixels of the X-ray detector. Anti-scatter grids of this type bring about an almost perfect suppression of scattered radiation, though such anti-scatter grids are always recognizable in the reconstructed X-ray image. However, the anti-scatter grids may be removed from the X-ray image by a calibration process and subtraction. This approach requires an increased pre- or postprocessing overhead. Moreover, this approach has been restricted in the past to static systems because the calibration is position- or orientation-dependent and also specific to a defined distance between X-ray beam source and X-ray detector.

A third solution proposes a uniform movement of the anti-scatter grid according to the second proposal relative to the X-ray detector during the projection data acquisition. In this way, the absorption of unscattered X-ray radiation is spatially (e.g., evenly) distributed, and the anti-scatter grid is no longer recognizable in the reconstructed X-ray image. This approach may be applied in acquisitions in which only one X-ray image is acquired by an X-ray pulse activated over a defined time. In order to achieve an almost complete compensation for the intensity modulation, the movement of the anti-scatter grid is to be exactly uniform. For this purpose, a counterweight moving counter to the anti-scatter grid is to be provided. Approaches using a periodically oscillating pendulum or circular (e.g., wormlike) movement require a complex structure, but hitherto have failed to demonstrate sufficient quality.

SUMMARY AND DESCRIPTION

The scope of the present invention is defined solely by the appended claims and is not affected to any degree by the statements within this summary.

The present embodiments may obviate one or more of the drawbacks or limitations in the related art. For example, the disadvantages of the prior art are overcome, and an anti-scatter grid by which a higher image quality may be achieved in relation to a wide range of applications is provided.

The present embodiments relate, in a first aspect, to an anti-scatter grid for an X-ray beam detector including a plurality of X-ray absorption plates and a carrier body to which the plurality of X-ray absorption plates are fastened.

In this arrangement, the carrier body is embodied in a meander shape having a plurality of linearly extending subsections and curve sections connecting these with one another. At least one X-ray absorption plate is arranged in each linearly extending subsection.

The carrier body is embodied to provide a fixing and/or a mechanical support or stabilization of the X-ray absorption plates in a desired arrangement or orientation and/or to effect a desired clearance.

The carrier body is embodied in a meander shape (e.g., features a wavelike or sinus-like profile). The carrier body is embodied essentially as a body that is elongated in one spatial dimension and, in contrast thereto, as narrow in at least one second spatial dimension. This shape of the carrier body permits simple mechanical processing. The meander shape of the carrier body is achieved, for example, by a bending process. The meander shape includes rectilinear (e.g., non-bent or non-curved subsections) and bent or curved curve sections incorporated into the carrier body along a longest extension direction.

The linearly extending subsections are, for example, embodied and large enough to accommodate in each case at least two X-ray absorption plates.

The X-ray absorption plates may, for example, be affixed to the carrier body (e.g., by adhesive bonding).

The X-ray absorption plates are embodied to absorb X-ray radiation and, for example, X-ray radiation scattered by an examination subject (e.g., scattered radiation). Accordingly, the X-ray absorption plates consist of a material that is characterized by a high X-ray quantum absorption efficiency. Suitable candidates as material for the X-ray absorption plates include, for example, copper, tungsten or another heavy metal. An alloy including one of the cited materials may also be employed. In order to achieve a plate- or lamella-like shape, this material is embodied as significantly narrower in one spatial dimension than in the two other spatial dimensions. The X-ray absorption plates may be approximately 0.1 mm thick.

In an embodiment, the linearly extending subsections run parallel to one another at least in certain areas, and the respective adjacent X-ray absorption plates arranged in the area embody a radiation channel for X-ray radiation. In other words, the curve sections may accomplish a change of direction lying in the range of or exactly at 360°. In this way, a parallel or approximately parallel arrangement of the X-ray absorption plates disposed in the subsections is achieved. The linear subsections as well as the X-ray absorption plates arranged therein therefore extend substantially parallel to one another at least in certain areas, and, for example, also parallel to an X-ray beam propagation direction. In this way, respective adjacent X-ray absorption plates (e.g., lying directly next to one another) form a radiation channel in the area. This effects an absorption of the majority of the scattered radiation, with X-ray radiation not scattered by the examination subject being able to pass almost unobstructed through the anti-scatter grid.

"In certain areas" may be that outside of the area having a substantially parallel subsection profile, there may also be parts of the anti-scatter grid in which the linear subsections do not run in parallel.

Alternatively, it may be provided that the carrier body and the X-ray absorption plates are embodied as a physical unit, and the X-ray absorption plates are formed in the linearly extending subsections by the carrier body itself. In this embodiment, the entire carrier body is formed by a material that may be utilized for the X-ray absorption plates.

In another embodiment, the carrier body is embodied as a single, integral unit or in two parts. In the embodiment variant in the form of a single, integral unit, the carrier body is embodied such that the X-ray absorption plates bear with a corresponding base area on the planar surface of the linearly extending subsections. In this embodiment, a linearly extending subsection may accommodate two X-ray absorption plates in each case, and on opposite sides. In the two-part embodiment, the carrier body is embodied from two substantially wire-shaped or ribbon-cable-shaped individual bodies. Both individual bodies have the same meander shape. The X-ray absorption plates are arranged on opposite sides in each case with a subsection of the congruently arranged individual bodies and fastened thereto by, for example, an adhesive bonding process. In other words, only the X-ray absorption plates establish a physical connection between the two individual bodies in this embodiment. In this embodiment, precisely one X-ray absorption plate is arranged in each subsection of the anti-scatter grid. While the embodiment formed as a single, integral unit offers a more straightforward manufacturing process, a disadvantageous absorption of unscattered X-ray radiation by the carrier body may be largely avoided as a result of the saving of material in relation to the carrier body in the case of the two-part embodiment.

In a further embodiment, the carrier body is formed from metal or a polymer. In an embodiment, the carrier body consists of the same material as the X-ray absorption plates. This further simplifies the manufacturing process.

In another embodiment, the X-ray absorption plates have an extension of 15 mm to 25 mm in the X-ray beam propagation direction. This extension corresponds to the length or depth of the radiation channels formed by the X-ray absorption plates. A length/depth of precisely 2 mm is sufficient, for example, in the case of X-ray absorption plates made of tungsten or tungsten alloys in order to bring about a satisfactory suppression of scattered radiation upstream of the X-ray detector. Other extensions of the X-ray absorption plates are likewise possible.

In a further embodiment, the carrier body is embodied as movable substantially perpendicularly to the X-ray absorption plates. For example, the carrier body is movable perpendicularly to the X-ray absorption plates arranged parallel to one another at least in certain areas. The movement may be accomplished during a recording or acquisition of X-ray projection measurement data. As a result of this, an undesirable intensity modulation of the X-ray radiation detected by the X-ray beam detector may be suppressed.

The movement that the carrier body is to be able to accomplish may cause deformations of the carrier body. To provide that the movement causes no damage to the anti-scatter grid, it is provided in a further embodiment that the carrier body is embodied as elastically deformable at least in curve sections. Elastic deformability provides that the carrier body may assume a different, modified shape when force is applied, yet autonomously resumes an original shape when no force is applied. In other words, the curve sections of the carrier body may be embodied as elastically deformable at least temporarily and, in certain areas, during the movement (e.g., during movement of the carrier body), may include a different angle (e.g., a smaller angle than 360°).

In another embodiment, the carrier body runs on a closed path. In other words, the carrier body has no beginning and no end, or these are joined to one another (e.g., in a stepless or seamless manner). In this embodiment, the carrier body is equipped uniformly over an entire course with subsections and X-ray absorption plates. This embodiment is suitable for a uniform movement of the anti-scatter grid, as will be described with reference to the following embodiment.

In this embodiment, the anti-scatter grid also includes two roller bodies. Each of the two roller bodies is rotatable about an axis of rotation. The two axes of rotation lie parallel to one another. The carrier body extends circumferentially around the two roller bodies. The carrier body bears with internal curve sections of the carrier body at least partially on the roller bodies and is movable by rotation of the roller bodies. The two roller bodies may be embodied in a wheel or cylinder shape. The two roller bodies may have the same diameter. In other words, a simultaneous rotational movement of the two roller bodies causes a driving force to be applied to the anti-scatter grid, which is consequently set into a uniform motion that extends substantially perpendicularly to the base area of the X-ray absorption plates aligned in parallel in certain areas. This embodiment permits a steady, uninterrupted movement of the carrier body since the movement is performed in one movement direction only. The embodiment makes counterweights and compensation movements of the counterweights superfluous and is accordingly stable and resistant to failure.

In an embodiment, the carrier body extends at least in certain areas between two roller bodies on or along a curved trajectory. The curvature of the trajectory is embodied as convex in relation to an X-ray beam direction of incident X-ray radiation. The carrier body may be maintained on the curved trajectory, for example, by a guiding element in the form of a guide rail. Using an elastic deformation of the carrier body (e.g., of the curve sections) in this area too, it is possible for the radiation channels embodied by the X-ray absorption plates to be aligned to the X-ray beam direction of incident X-ray radiation (e.g., to be oriented parallel thereto). This makes the present embodiments particularly well suited to application with X-ray imaging systems that produce a fan-shaped X-ray beam.

In one embodiment, the radius of the curved trajectory is variable. In other words, the radius of curvature of the trajectory may be varied. The radius of curvature may be adjusted, for example, to a variable distance between X-ray beam source and X-ray beam detector, where the alignment of the radiation channels to the X-ray beam direction of the incident X-ray radiation may be maintained. This is typical, for example, in the case of a C-arm X-ray device during an examination.

The radius of curvature of the trajectory may be realized, for example, by an elastically deformable guide rail, the radius of curvature of which is automatically adjusted (e.g., taking into account a current distance between X-ray beam detector and X-ray beam source). Alternatively, a plurality of guide rails may be provided. Each guide rail of the plurality of guide rails has radii of curvature differing from one another that may be interchanged automatically, as required.

In order to increase the stability of the anti-scatter grid further, a retaining device that extends circumferentially around the carrier body and supports the carrier body in shape or in the course of movement may be provided. The retaining device may be embodied, for example, as a stabilizing elastic band.

In another embodiment, the roller bodies are embodied to drive the carrier body such that the X-ray absorption plates move at a speed in the range of 0.3 m/s to 10 m/s. The achieved movement is a movement in one direction, with no reversal of direction taking place. In this case, the carrier body runs at a constant speed around the two roller bodies. A constant speed in the specified area provides that the anti-scatter grid is no longer or scarcely still recognizable in a reconstructed X-ray image.

In one embodiment, the X-ray absorption plates are spaced apart from one another at a distance in the range of 200 µm to 3000 µm. In conjunction with the above-cited speed of movement, this results in an optimal suppression of the visibility of the anti-scatter grid in a reconstructed X-ray image.

Another aspect relates to an X-ray beam detector for a medical X-ray imaging system including an anti-scatter grid according to one or more of the present embodiments. The X-ray beam detector may be embodied as a detector for X-rays that converts incident X-rays directly or indirectly into an electrical signal. The X-ray detector may be a flat-panel detector, but also a curved detector (e.g., a detector having a curved detection surface).

In an embodiment, the X-ray beam detector is embodied in the form of an X-ray flat-panel detector that also includes a sensor element that is arranged between the two roller bodies of the anti-scatter grid and is positioned after the X-ray absorption plates in the X-ray beam direction such that X-ray radiation impinges on the sensor element after the X-ray radiation has passed through the anti-scatter grid.

A medical X-ray imaging system including an anti-scatter grid according to one or more of the present embodiments is also provided. The X-ray imaging system may be embodied as, for example, a fluoroscopic X-ray machine, a C-arm X-ray device, an angiography system, a mammography system, a computed tomography system, or the like.

BRIEF DESCRIPTION OF THE DRAWINGS

The above-described characteristics, features, and advantages of this invention, as well as the manner in which these are realized, will become clearer and more readily understandable in conjunction with the following description of the exemplary embodiments, which are explained in more detail in connection with the drawings. No limitation of the invention to the exemplary embodiments is implied by this description. Like components are labeled with the same reference signs in the various figures. The figures are generally not to scale. In the figures.

DETAILED DESCRIPTION

Figure 1:
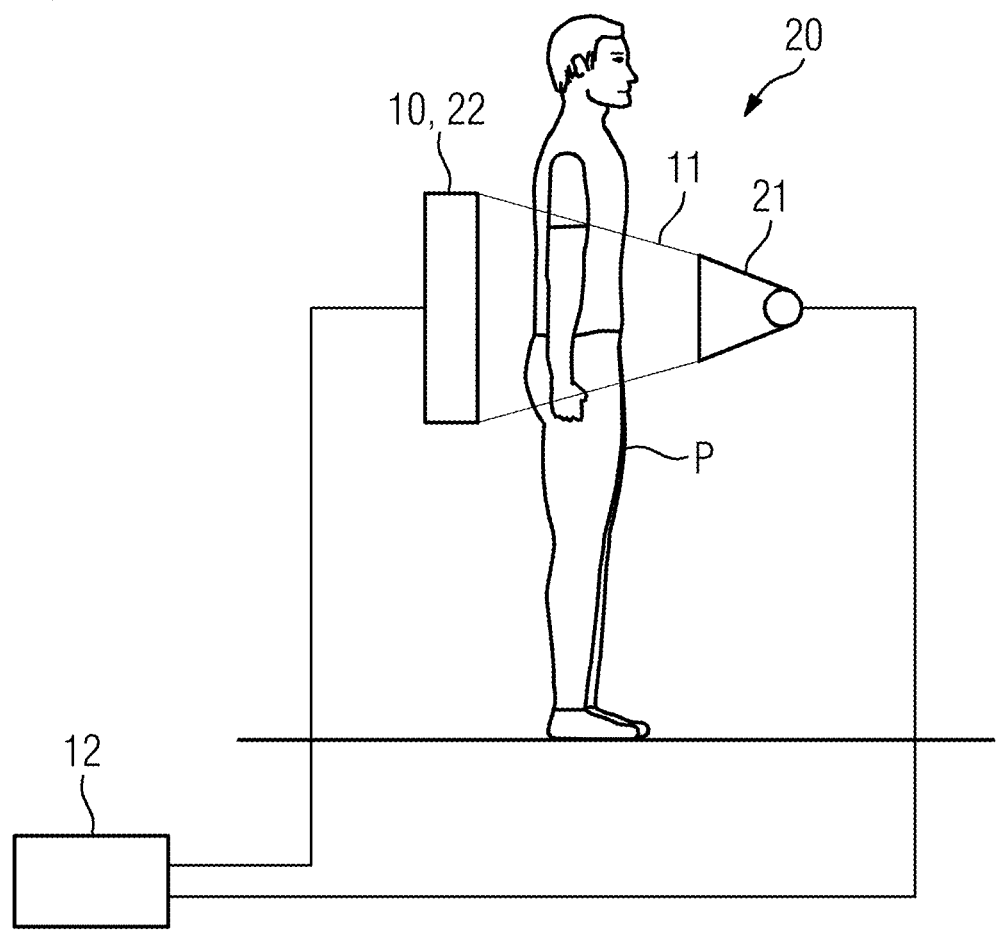
FIG. 1 shows an X-ray imaging system in a greatly simplified embodiment.

FIG. 1 shows a very simplified representation of an X-ray imaging system 20 in an embodiment. The X-ray imaging system 20 includes an X-ray beam source 21 and, arranged opposite the X-ray beam source 21, an X-ray beam detector 22 in the form of an indirectly converting X-ray beam detector. The X-ray beam source 21 and the X-ray beam detector 22 may be mounted movably relative to one another or arranged in a fixed position opposite one another. The X-ray beam source 21 is configured to transmit an X-ray beam 11 during operation of the X-ray imaging system. In this instance, the X-ray beam 11 is actually formed by a fan beam, though the X-ray beam 11 may also be embodied as a conical beam. The individual partial beams of the X-ray beam 11 are emitted by the X-ray beam source 21 as radial beams, which indicates the X-ray beam direction (e.g., original X-ray beam direction) for each of the radial beams (e.g., in the manner of a radial pointer). The X-ray beam detector 22 is in this case embodied as flat such that each of the radial beams is incident normally or at least approximately normally on an X-ray-sensitive surface (not shown in further detail) or a planar sensor element 6 of the X-ray beam detector 22. In order to control the X-ray beam source 21 and to evaluate an intensity distribution of the X-ray beam 11 detected by the X-ray beam detector 22, the X-ray beam source 21 and the X-ray beam detector 22 are connected to a control computer 12 for signal transmission purposes.

During operation of the X-ray unit 1, the X-ray beam 11 or partial X-ray beams of the X-ray beam 11 are also scattered by a measurement or examination subject P (e.g., a patient) arranged in the beam path of the X-ray beam 11 into scattered rays diverging from the original X-ray beam direction (not shown in more detail), for which reason the X-ray beam detector 22 has an anti-scatter grid 10 having X-ray absorption surfaces 8 that are positioned in front of an X-ray-sensitive detector surface 6 of the X-ray beam detector 22. This anti-scatter grid 10 covers the entire X-ray-sensitive detector surface 6. The anti-scatter grid 10 is in this case structured and arranged such that the scattered rays diverging from the X-ray beam direction are "intercepted" and, at least as far as possible, only the partial X-ray beams of the X-ray beam 11 running or approximately running in the X-ray beam propagation direction may impinge on the X-ray-sensitive surface of the X-ray beam detector 22.

Figure 2:
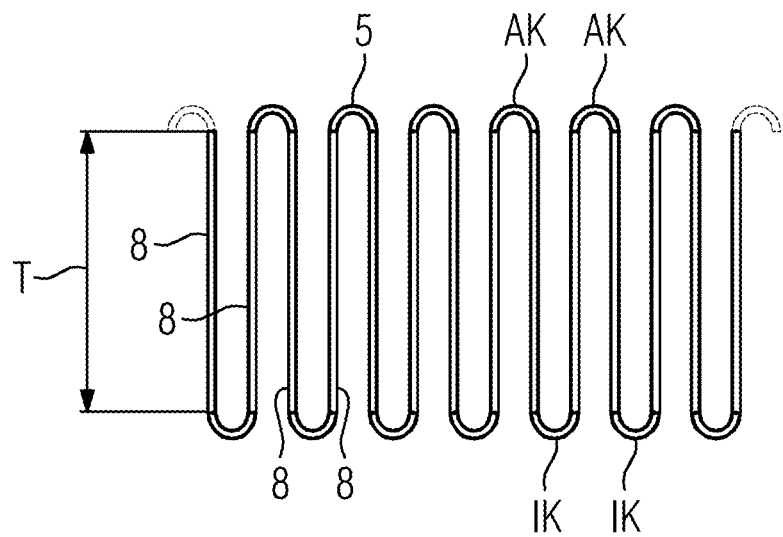
FIG. 2 shows a side view of an anti-scatter grid in an embodiment.

FIG. 2 shows a side view of an anti-scatter grid 10 in an embodiment.

Figure 3:
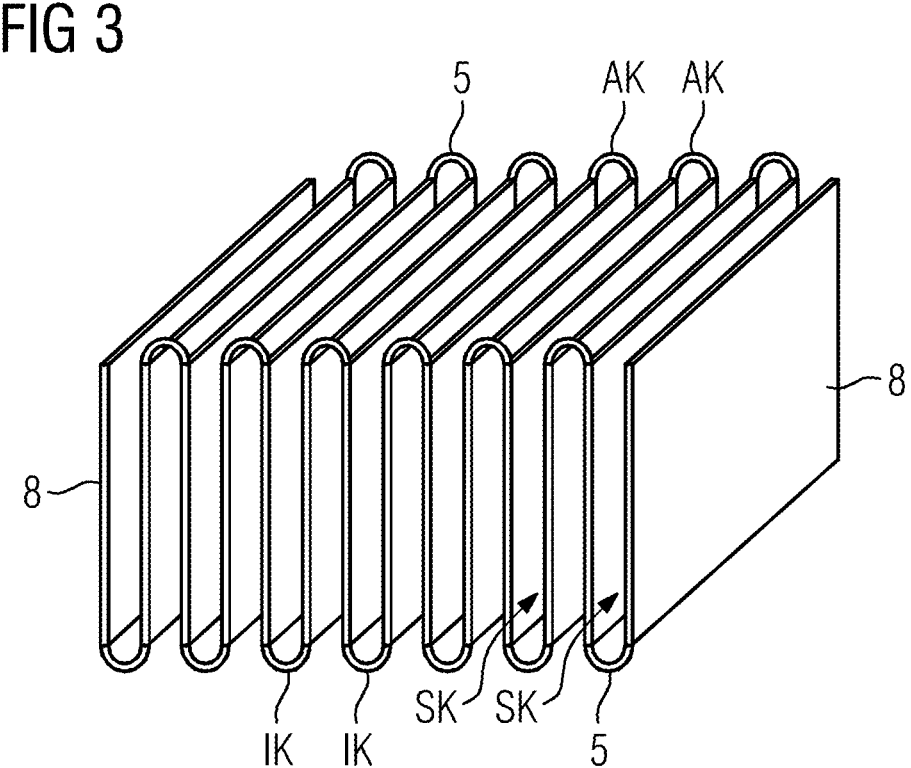
FIG. 3 shows a perspective view of the anti-scatter grid in the same embodiment.

FIG. 3 shows a perspective view of the anti-scatter grid 10 in the same embodiment.

The anti-scatter grid 10 includes a plurality of X-ray absorption plates 8 and a carrier body 5 to which the plurality of X-ray absorption plates 8 are fastened. The carrier body 5 is embodied in a meander shape with a plurality of linearly extending subsections T and curve sections IK, AK connecting these with one another. The plurality of X-ray absorption plates 8 are arranged in the subsection T extending in a straight line. At least one X-ray absorption plate 8 of the plurality of X-ray absorption plates 8 is provided per subsection T. The meander shape of the carrier body 5 is characterized in that the linearly extending subsections T run parallel to one another at least in certain areas, and respective adjacent X-ray absorption plates 8 arranged therein form a radiation channel SK for X-ray radiation. In the embodiment shown, the carrier body 5 is formed in two parts. In this, the carrier body includes two individual bodies that are embodied substantially as two meander-shaped wires (e.g., ribbon wires). The X-ray absorption plates 5 are adhesively bonded on narrow sides of the X-ray absorption plates 5 to the individual bodies, and in this way, establish a connection between the individual bodies. In this embodiment, each subsection T of the carrier body 5 includes precisely one X-ray absorption plate 8, both sides of the same in each case forming an X-ray beam absorbing wall of two adjacent radiation channels SK.

Alternatively, the carrier body 5 may also be embodied as a single, integral unit. The X-ray absorption plates 8 are then joined (e.g., adhesively bonded) over surfaces of the X-ray absorption plates 8 to a subsection T. In this case, each subsection T includes two X-ray absorption plates 8.

In a further alternative, the carrier body may form a physical unit with the X-ray absorption plates 8, where the linearly extending subsections themselves constitute the X-ray absorption plates. In this embodiment, the entire carrier body 5 may be formed from X-ray radiation absorbing material.

The X-ray absorption plates 8 may consist, for example, of tungsten or other heavy metals, or of alloys or material compositions including these elements. The carrier body 5 may consist of a material including a polymer or a metal.

The X-ray absorption plates 8 of the anti-scatter grid 10 have an extension of 15 mm to 25 mm in the X-ray beam propagation direction. This length corresponds to the length of the embodied radiation channels SK. This length has proven appropriate in practical trials for achieving an adequate suppression of scattered radiation.

The carrier body 5 is embodied as movable substantially perpendicularly to the X-ray absorption plates 8. In other words, a movement of the carrier body 5 together with X-ray absorption plates 8 along the surface normal of the sides of the X-ray absorption plates 8 forming the walls of a radiation channel SK is provided in order to suppress a locally defined intensity modulation caused by the anti-scatter grid during a protracted X-ray image acquisition.

In arrangement of the X-ray absorption plates 8 on the carrier body 5, the X-ray absorption plates 8 may be spaced apart from one another at a distance in the range of 200 μm to 3000 μm. This clearance produces a suppression of the visibility of the anti-scatter grid in X-ray images. In conjunction with a thickness of the absorption plates of 0.1 mm, different characteristics of the anti-scatter grid may be set.

For a transmission rate of unscattered X-ray radiation, the smaller the spacing of the X-ray absorption plates 8, the lower is the proportion of transmitting unscattered X-ray photons. For example, at a spacing of 0.2 mm, only about 50% of the unscattered X-ray photons reach the X-ray beam detector, whereas this rises to about 95% at a spacing of 2 mm.

For a necessary movement speed of the carrier body 5, at a minimum X-ray pulse duration of, for example, 3 ms, the anti-scatter grid 10 may move at least a distance corresponding to the width of one radiation channel (e.g., 0.2 mm to 3 mm). At 0.2 mm, a minimum speed of 0.06 m/sec is required, for example. Generally, a faster movement of the anti-scatter grid in which multiple adjacent scattered radiation channels SK overlap during one pulse duration is more advantageous, since in this way, geometric irregularities of the anti-scatter grid may be compensated for in addition.

Figure 4:
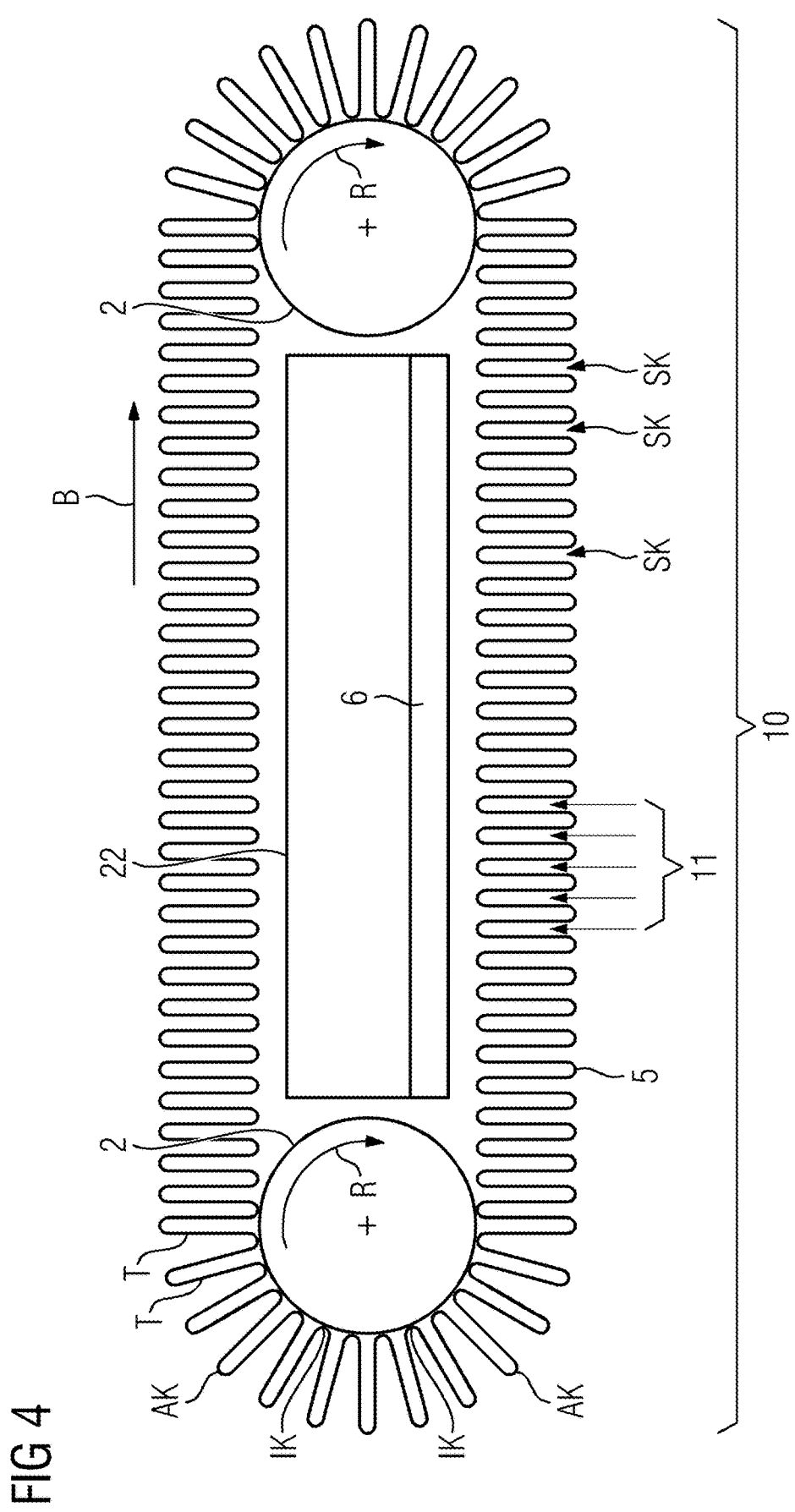
FIG. 4 shows a detail view of an X-ray beam detector in an embodiment variant.

FIG. 4 shows an X-ray beam detector 22 in a detail view of an embodiment variant. The X-ray beam detector 22 includes an anti-scatter grid 10 according to one or more of the present embodiments. In this embodiment, the carrier body 5 extends on a closed path; in other words, the carrier body 5 has no beginning and no end. The closed path of the carrier body 5 at least partially encompasses the X-ray beam detector 22, the sensor element 6, for example, lying within the closed path. The X-ray detector 22 may include further functional units or components. The anti-scatter grid 10 further includes at least two roller bodies 2. Each of the at least two roller bodies 2 is rotatable about an axis of rotation and includes an axis of rotation (e.g., points in the roller bodies). Two roller bodies 2 are shown. The two axes of rotation are arranged parallel to each other. The carrier body 5 or a closed path of the carrier body 5 runs circumferentially around the two roller bodies 2. In this arrangement, the carrier body 5 bears with internal curve sections IK at least partially circumferentially on the roller bodies 2. The roller bodies 2 are mounted so as to be rotatable (indicated by the arrow in the roller body) about axes of rotation of the roller bodies 2, respectively. The movement of the roller bodies 2 enables the carrier body 5 to be driven in a movement direction B. In the exemplary embodiment shown, the roller bodies 2 are embodied to drive the carrier body 5 such that the X-ray absorption plates 8 arranged on the carrier body move at a speed in the range of 0.3 m/s to 10 m/s in the movement direction B. The movement of the carrier body 5 runs substantially perpendicularly to the X-ray absorption plates 8. At the circumferences of the roller bodies 2, the carrier body 5 accomplishes a change in direction of 360°. In order to realize this change of direction, the carrier body 5 is embodied as elastically deformable at least in curve sections AK, IK. In other words, the meander shape of the carrier body may be elastically deformed in the curve sections.

For example, in X-ray imaging systems producing a fan-shaped X-ray beam, it may be provided that the carrier body 5 runs along a curved trajectory between the two roller bodies 2 at least in certain areas. The curvature of the trajectory is embodied as convex in relation to an X-ray beam direction of incident X-ray radiation (e.g., the fan beam in this case). The carrier body 5 may be maintained on the curved trajectory in this area (e.g., by a guiding element in the form of a guide rail). By an elastic deformation of the carrier body (e.g., of curve sections), the radiation channels are aligned in this area to the X-ray beam direction of the incident fan-shaped X-ray radiation, with the result that the unscattered X-ray photons may pass substantially unobstructed through a radiation channel. In one embodiment, the radius of the curved trajectory may be adjustable (e.g., selectable or variable), so that the radius of curvature may be matched to a variable distance between X-ray beam source and X-ray beam detector without at the same time changing the parallel alignment of the radiation channels to the X-ray beam direction of the incident X-ray radiation and thereby minimizing the permeability for unscattered X-ray photons. The radius of curvature of the trajectory may be realized, for example, by an elastically deformable guide rail, the radius of curvature of which is adjusted automatically (e.g., taking into account a current distance between X-ray beam detector and X-ray beam source). Alternatively, a plurality of guide rails may be provided, each having radii of curvature differing from one another, which may be interchanged automatically, as required. This makes the anti-scatter grid 10, for example, suitable also for application using variable angulation of the X-ray imaging system during an image data acquisition session.

Although the invention has been illustrated and described in greater detail based on the exemplary embodiments, the invention is nonetheless not limited by the disclosed examples, and other variations may be derived herefrom by the person skilled in the art without leaving the scope of protection of the invention.

The elements and features recited in the appended claims may be combined in different ways to produce new claims that likewise fall within the scope of the present invention. Thus, whereas the dependent claims appended below depend from only a single independent or dependent claim, it is to be understood that these dependent claims may, alternatively, be made to depend in the alternative from any preceding or following claim, whether independent or dependent. Such new combinations are to be understood as forming a part of the present specification.

While the present invention has been described above by reference to various embodiments, it should be understood that many changes and modifications can be made to the described embodiments. It is therefore intended that the foregoing description be regarded as illustrative rather than limiting, and that it be understood that all equivalents and/or combinations of embodiments are intended to be included in this description.

The invention claimed is:

1. An anti-scatter grid for an X-ray beam detector, the anti-scatter grid comprising:
    a plurality of X-ray absorption plates; and
    a carrier body to which the plurality of X-ray absorption plates are fastened,
    wherein the carrier body is configured in a meander shape with a plurality of linearly extending subsections and curve sections connecting the plurality of linearly extending subsections with one another, wherein the carrier body is configured as elastically deformable at least in the curve sections, and
    wherein at least one X-ray absorption plate of the plurality of X-ray absorption plates is arranged in each linearly extending subsection of the plurality of linearly extending subsections.

2. The anti-scatter grid of claim 1, wherein the plurality of linearly extending subsections run parallel to one another at least in certain areas, and respective adjacent X-ray absorption plates of the plurality of X-ray absorption plates arranged therein form a radiation channel for X-ray radiation.

3. The anti-scatter grid of claim 1, wherein the carrier body is configured as a single, integral unit or in two parts.

4. The anti-scatter grid of claim 1, wherein the carrier body is formed from metal or a polymer.

5. The anti-scatter grid of claim 1, wherein the plurality of X-ray absorption plates have an extension in the range of 15 mm to 25 mm in a X-ray beam propagation direction.

6. The anti-scatter grid of claim 1, wherein the carrier body is configured as movable substantially perpendicularly to the plurality of X-ray absorption plates.

7. The anti-scatter grid of claim 1, wherein the carrier body runs on a closed path.

8. The anti-scatter grid of claim 7, further comprising at least two roller bodies,
    wherein each of the at least two roller bodies is rotatable about an axis of rotation,
    wherein the two axes of rotation lie parallel to one another, and the carrier body extends circumferentially around the at least two roller bodies, and
    wherein the carrier body bears with internal curve sections of the carrier body at least partially on the at least two roller bodies and is movable by rotation of the at least two roller bodies.

9. The anti-scatter grid of claim 8, wherein the carrier body runs on a curved trajectory between two roller bodies of the at least two roller bodies at least in certain areas, and
    wherein a curvature of the curved trajectory is configured as convex in relation to an X-ray beam direction of incident X-ray radiation.

10. The antiscatter grid of claim 9, wherein a radius of the curved trajectory is variable.

11. The anti-scatter grid of claim 8, wherein the at least two roller bodies are embodied to drive the carrier body such that the plurality of X-ray absorption plates move at a speed in a range of 0.3 m/s to 10 m/s.

12. The anti-scatter grid of claim 1, wherein the plurality of X-ray absorption plates are spaced apart from one another at a distance in a range of 200 μm to 3000 μm.

13. An X-ray beam detector for a medical X-ray imaging system, the X-ray beam detector comprising:
    an anti-scatter grid comprising:
        a plurality of X-ray absorption plates; and
        a carrier body to which the plurality of X-ray absorption plates are fastened,
        wherein the carrier body is configured in a meander shape with a plurality of linearly extending subsections and curve sections connecting the plurality of linearly extending subsections with one another, wherein the carrier body is configured as elastically deformable at least in the curve sections, and wherein at least one X-ray absorption plate of the plurality of X-ray absorption plates is arranged in each linearly extending subsection of the plurality of linearly extending subsections.

14. The X-ray beam detector of claim 13, wherein the X-ray beam detector is in the form of an X-ray flat-panel detector, wherein the X-ray beam detector further comprises a sensor element that is arranged between two roller bodies of the anti-scatter grid such that X-ray radiation impinges on the sensor element after the X-ray radiation has passed through the anti-scatter grid.

15. A medical X-ray imaging system comprising:

an anti-scatter grid for an X-ray beam detector, the anti-scatter grid comprising:
- a plurality of X-ray absorption plates; and
- a carrier body to which the plurality of X-ray absorption plates are fastened, wherein the carrier body is configured in a meander shape with a plurality of linearly extending subsections and curve sections connecting the plurality of linearly extending subsections with one another, wherein the carrier body is configured as elastically deformable at least in the curve sections, and wherein at least one X-ray absorption plate of the plurality of X-ray absorption plates is arranged in each linearly extending subsection of the plurality of linearly extending subsections.

* * * * *